United States Patent [19]

Daniel et al.

[11] Patent Number: 4,712,542
[45] Date of Patent: Dec. 15, 1987

[54] SYSTEM FOR ESTABLISHING LIGAMENT GRAFT ORIENTATION AND ISOMETRY

[75] Inventors: Dale M. Daniel, Lamesa; Kay R. Watkins, San Diego, both of Calif.

[73] Assignee: Medmetric Corporation, San Diego, Calif.

[21] Appl. No.: 880,055

[22] Filed: Jun. 30, 1986

[51] Int. Cl.$^4$ .............................................. A61F 5/04
[52] U.S. Cl. ............................ 128/92 V; 128/92 VK; 623/13
[58] Field of Search ............ 128/92 VD, 92 V, 92 R, 128/92 VL, 92 VK, 303 R; 623/13, 20

[56] References Cited

U.S. PATENT DOCUMENTS

| | | | |
|---|---|---|---|
| 1,347,579 | 7/1920 | Henrikson | 128/92 VK |
| 1,822,352 | 9/1931 | Laursen | 73/143 |
| 2,337,629 | 12/1943 | Shortell | 29/73 |
| 2,516,079 | 7/1950 | Shortell | 29/73 |
| 2,590,498 | 3/1952 | Bomberger | 73/143 |
| 3,016,741 | 1/1962 | Kulp | 73/143 |
| 3,432,930 | 3/1969 | Ljungberg | 33/137 |
| 3,696,667 | 10/1972 | Foster et al. | 73/143 |
| 3,896,500 | 7/1975 | Lambert et al. | 128/92 YF |
| 3,953,896 | 5/1976 | Treace | 128/92 YF |
| 3,973,277 | 8/1976 | Semple et al. | 128/92 YF |
| 3,976,060 | 8/1976 | Hildebrandt et al. | 128/92 R |
| 4,024,860 | 5/1977 | Chelnokov et al. | 128/92 A |
| 4,050,464 | 9/1977 | Hall | 128/303 R |
| 4,220,146 | 9/1980 | Cloutier | 128/69 |
| 4,246,660 | 1/1981 | Wevers | 128/92 YF |
| 4,317,377 | 3/1982 | Wrinkle | 73/862.42 |
| 4,364,389 | 12/1982 | Keller | 128/303 R |
| 4,501,266 | 2/1985 | McDaniel | 128/69 |

Primary Examiner—C. Fred Rosenbaum
Assistant Examiner—C. W. Shedd
Attorney, Agent, or Firm—Fulwider, Patton, Rieber, Lee & Utecht

[57] ABSTRACT

A method and instrument for skeletal referenced isometric positioning and tensioning of a ligament graft, particularly during knee surgery involving the anterior cruciate and the posterior cruciate ligaments. The graft is extended from one fixation site and attached to a sled slidably carried by a frame which is skeletally mounted to the other fixation site. A thumb nut and lead screw assembly on the skeletally fixed frame is operative to compress a spring in the sled and move the sled in a direction effective to tension the graft. Isometry is achieved when the relative positions of the frame and sled indicate constant graft tension and displacement through the entire range of passive knee flexion. The sled can be fixed relative to the frame for evaluation of joint laxity.

15 Claims, 17 Drawing Figures

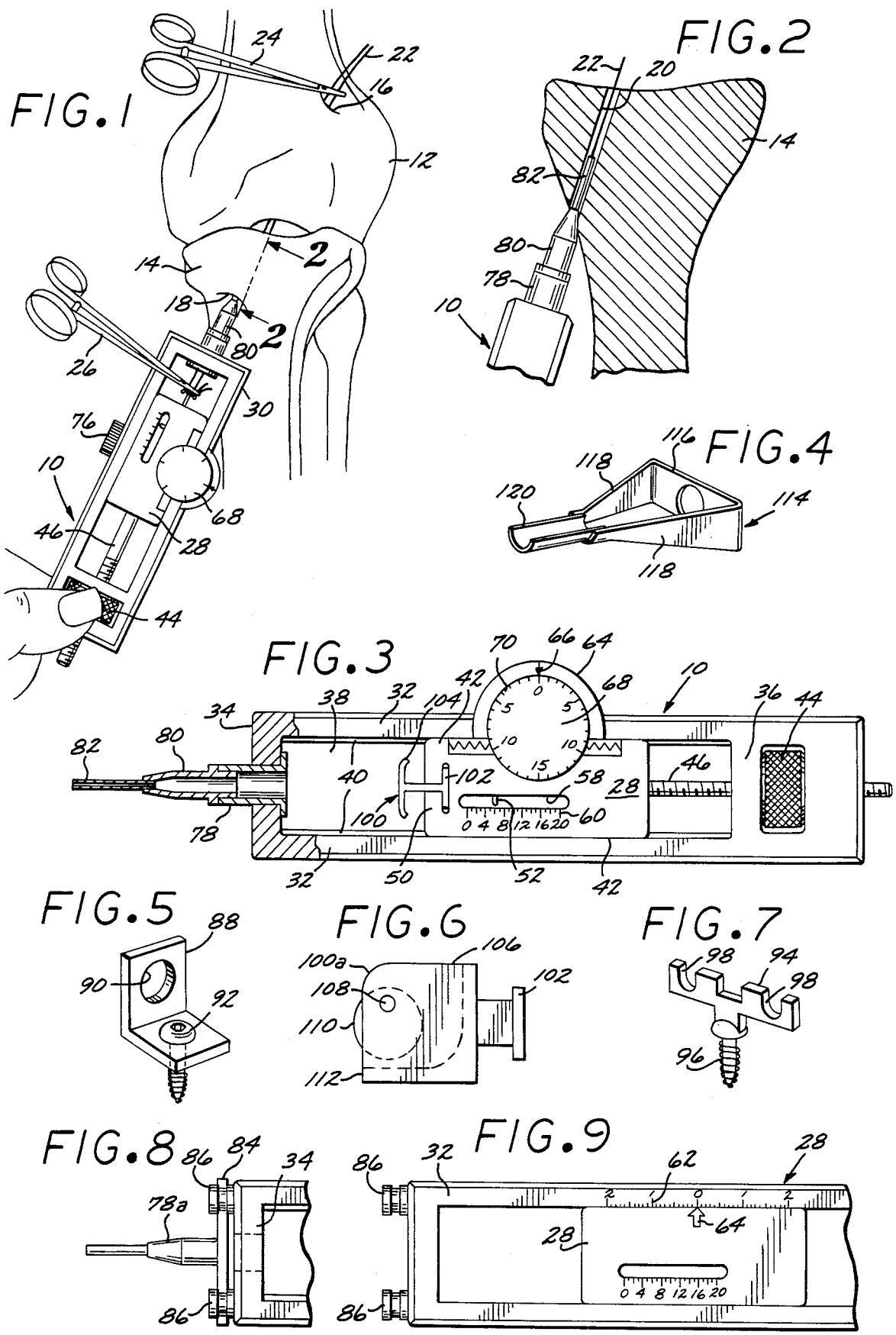

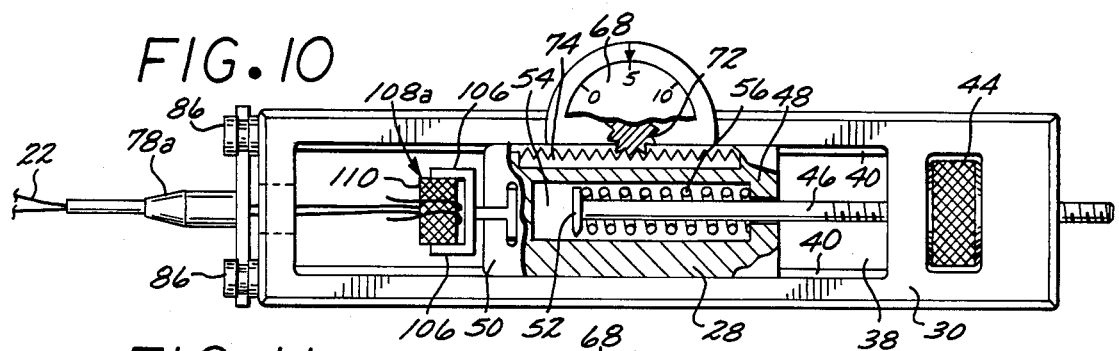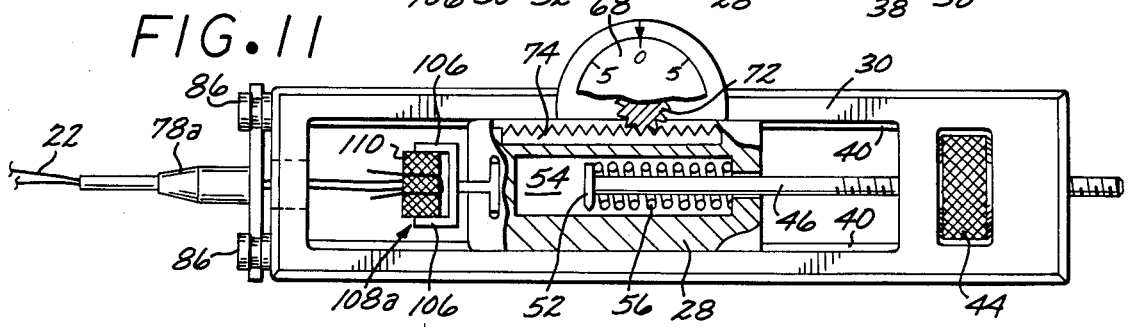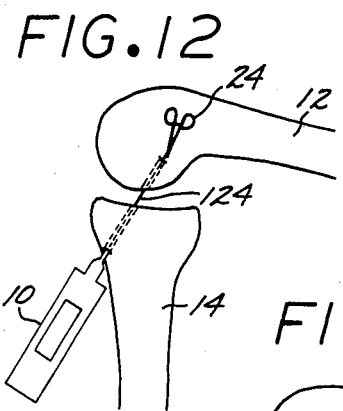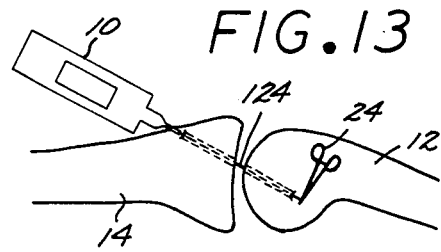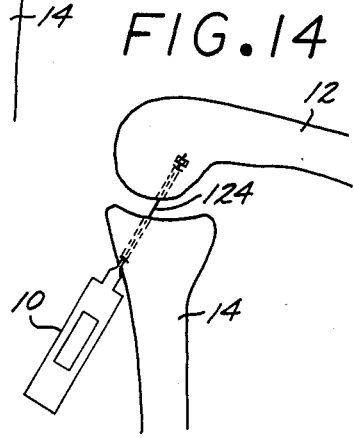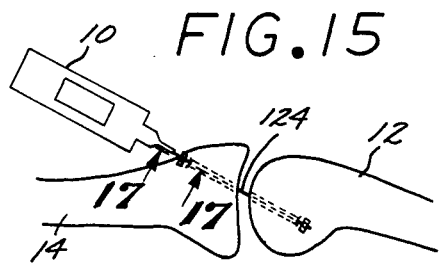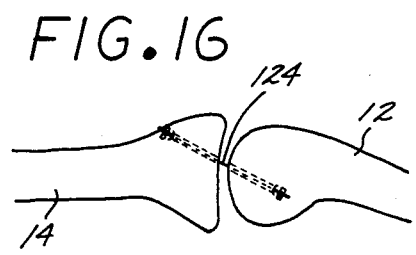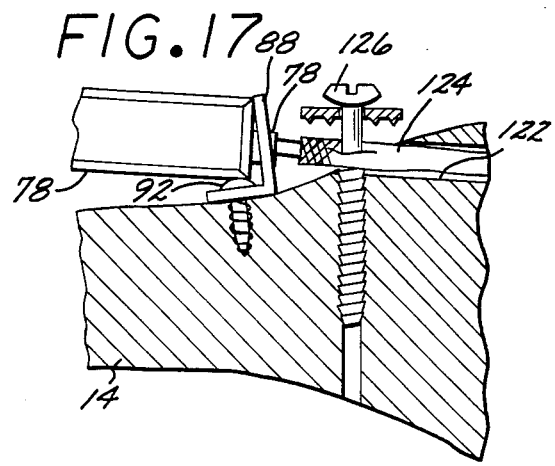

SYSTEM FOR ESTABLISHING LIGAMENT GRAFT ORIENTATION AND ISOMETRY

BACKGROUND OF THE INVENTION

1. Field of the Invention

The present invention relates to a skeletal referenced method and instrument for establishing ligament graft tension and isometry, particularly during knee surgery involving the cruciate ligaments.

2. Description of the Prior Art

Although the present method and instrument have general application to proper orientation of a ligament graft between fixation sites on adjacent articulated bone structures, they have particular application to reconstructive surgery of the anterior and posterior cruciate ligaments of the knee, and especially isometric positioning of autogenous or prosthetic anterior cruciate ligament grafts.

In addition to proper graft selection, tensioning and fixation, correct isometric positioning of the anterior cruciate ligament graft is important to minimize postoperative complications such as stiffness and residual pathologic laxity.

By definition, "isometrically" positioned grafts maintain a constant length and tension throughout passive knee motion or flexion. Graft isometry is dependent on proper graft orientation. Malpositioning of the cruciate ligaments can result in limitation of knee motion or more likely, elongation of the graft as it experiences different tensions at different knee positions. Various graft orientations are commonly used clinically in the prior art and there is a need for an interoperative instrument to aid in locating the path for isometric graft placement by precisely establishing expected graft tension and displacement changes prior to graft fixation.

Skeletal referenced tensioning after the isometric path has been established is a particularly important need. Tensioning using extra skeletal means, as is routinely now done, is uncertain because when the graft is fastened to the selected site of fixation a transfer of load causes translation of force to movement in the connective bone structure, producing change in the distance between fixation sites and tension reduction in the graft.

SUMMARY OF THE INVENTION

The method and instrument of the present invention are uniquely suited to establishment of proper skeletal referenced ligament graft tension and isometry, particularly during knee surgery involving the cruciate ligaments. According to the method, the surgeon selects the locations of the graft fixation sites based upon prior art studies of optimum graft fixation sites. In this regard, postero-superior positioned femoral fixation sites and associated femoral drill holes, and anteriorally positioned tibial fixation sites and associated drill holes, together with a socalled "over-the-top" orientation with deep cancellous bone trough in the lateral femoral condyle, has been found to best reproduce the normal anterior cruciate ligament isometry by allowing minimal graft length or tension changes with knee motion. The size of the femoral bone trough is dependent on the placement of the tibial fixation site or drill hole.

Upon selection of the graft fixation sites, the present method involves the drilling of suture openings in the femur and tibia, and location and skeletal fixation of the distal extremity of the frame of the instrument of invention adjacent one of the fixation sites, for example the tibial fixation site. A wire, drill guide or suture is disposed through the openings, it is fixed at one end to the femoral site and at its opposite end is fixed to a movable portion or sled of the instrument. The instrument sled includes means adapted to mount various attachments for temporary fixation. The instrument frame includes a distal nose means adapted to mount various tools or attachments to effect skeletal mounting of the frame adjacent rhe tibial site. The instrument sled includes a central cavity bounded by distal and proximal end walls, which houses a compression spring. A threaded thumb nut on the instrument frame is operative to advance a lead screw having an abutment element which is located adjacent the distal end wall of the sled cavity.

Rotation of the thumb nut in one direction moves the sled proximally to increase tension in the graft. Indicating means are on the frame and the sled indicate the longitudinal position of the sled relative to the frame, and further indicate the bias developed upon the sled, and consequently the level of tension in the graft. Use of the instrument to determine the existence of constant graft displacement and tension through a range of knee flexion confirms that the selected fixation sites are optimal. If not, the suture drill holes are reoriented and the procedure repeated until isometry is achieved.

The method involves enlarging the suture openings to provide graft holes in the femur and tibia extending between the established graft fixation sites. The graft is passed through the enlarged holes and fastened at the femoral fixation site by mechanical means to the femur. The opposite end is temporarily fastened to the distal end of the sled using the appropriate attachment. By rotation of the thumb nut tension is applied to the graft. By rotation of a locking thumb screw at the side of the frame the sled is prevented from movement simulating fixation. Knee flexion is repeated several times followed by laxity and knee rotating stability tests. The thumb screw is released and tension adjustment or final fixation at the tibia is performed.

The present instrument comes in either a lineal or a dial indicia version, either of which is able to show the position of the sled relative to the frame, and consequently the amount of graft displacement. Various attachments are provided to facilitate skeletal mounting of the instrument frame, including an attachment adapted for receipt in the tibial graft opening to achieve such skeletal mounting.

It is important to note that the instrument which develops and measures the tension in the ligament graft is skeletally fixed during ligament tensioning. Thus, in knee surgery involving the anterior cruciate ligament, once the graft is fixed to the femur, the graft tension which is developed by the instrument is developed with the instrument in abutment or skeletal fixation with the tibia. This preloads the connective bone structure such that after the graft is fixed at the tibia site, the tension developed and measured prior to the tibia site fixation will be the tension existing in the finally fixated ligament graft.

Other objects and features of the invention will become apparent from consideration of the following description taken in connection with the accompanying drawings.

BRIEF DESCRIPTION OF THE DRAWINGS

FIG. 1 is a perspective view of the present instrument as it would be used in testing for isometricity of the anterior cruciate ligament graft path in reconstructive knee surgery;

FIG. 2 is an enlarged sagittal section of the tibia with the instrument fitted with an attachment operatively positioned to accept a suture;

FIG. 3 is a top plan view, partially in section, illustrating the instrument of FIG. 1;

FIG. 4 is a detail perspective view of an instrument attachment for separably receiving a graft and skeletally mounting the instrument frame in operative position;

FIG. 5 is a detail perspective view of a bracket and cortical screw arrangement to effect skeletal mounting of the instrument frame;

FIG. 6 is a detail side elevational view of an alternate form of graft retaining attachment to be mounted to the instrument sled;

FIG. 7 is a detail perspective view of an alternate form of bracket and cortical screw means for skeletally fixing a modified form of instrument frame;

FIG. 8 is a partial side elevational view of the modified form of instrument frame adapted to accept the device of FIG. 7, and illustrating a modified form of suture nose for mounting on the modified instrument frame;

FIG. 9 is a partial top plan view of an instrument wherein the position of the sled relative to the instrument frame is indicated by linearly oriented indicia;

FIG. 10 is a top plan view, partially in longitudinal cross section, illustrating the sled bias means in a lightly loaded or compressed state;

FIG. 11 is a view similar to FIG. 10, but illustrating the sled bias means in a more heavily loaded or compressed state;

FIGS. 12 and 13 are schematic views illustrating the relationship of the instrument to the femur and tibia through the range of knee flexion during graft testing;

FIG. 14 is a schematic view similar to FIGS. 12 and 13, but illustrating permanent fixation of the graft at the femoral fixation site;

FIG. 15 is a schematic view similar to FIG. 14, but illustrating the positions of the femur and tibia at the point of permanent fixation of the graft at the tibial fixation site and before separation of the instrument from the graft;

FIG. 16 is a schematic view similar to FIG. 15, but illustrating the appearance of the graft after instrument separation; and FIG. 17 is an enlarged detail view of the device of FIG. 5 skeletally temporarily fixing the graft prior to final graft fixation to the tibial fixation site.

BRIEF DESCRIPTION OF THE PREFERRED EMBODIMENTS

Referring now to the drawings, and particularly to FIG. 1, an instrument 10 is illustrated in association with a femur 12 and tibia 14 characterized by proposed femoral and tibial graft fixation sites 16 and 18, respectively. After initial approximation of the locations of the sites 16 and 18, drill guide or wire or suture openings, such as the opening 20 seen in FIG. 2, are drilled in the femur and tibia between the sites 16 and 18. A tension element such as a wire cable or suture 22 is passed through the suture openings and the end of the suture 22 protruding through the lateral wall of the femur 12 is temporarily clamped or fixed against movement by a hemostat 24. The other end of the suture 22 is temporarily clamped or fixed by a hemostat 26 to a movable portion or sled 28 which is slidably carried by an elongated instrument body or frame 30. As will be seen, the frame 30 is skeletally fixed or mounted at its distal extremity adjacent the tibial fixation site 18, which is important to maintain the instrument frame 30 in a relatively fixed position so that movement of the sled 28 relative to the frame 30 can establish the amount of graft displacement and tensioning.

As seen in FIG. 3, the instrument frame 30 is generally rectangular and includes longitudinally extending, spaced apart side walls 32, an end wall 34 and a relatively thick end wall 36. The walls are spaced apart to define a rectangular internal space or sled opening 38.

Side walls 32 include integral rails 40 which longitudinally slidably support elongated side margins 42 of the sled 28. The sled 28 is longitudinally movable along the rails 40 by means of a thumb nut and lead screw arrangement. An adjusting thumb nut 44 is rotatably carried within a transverse opening provided in the instrument frame end wall 36, and an elongated lead screw 46 extends through a suitable longitudinal opening in the end wall 36. The screw 46 is in threadable engagement with the thumbwheel 44 and, as seen in FIG. 10, extends into the sled opening 38, through an opening in an end wall 48 of the sled 28, and into a central sled cavity 54. The sled 28 is longitudinally movable relative to the screw 46.

The free or sled end of the screw 46 fixedly mounts an abutment element or pointer 52 which is located adjacent an end wall 50 of the sled. The pointer 52 is thus located within the sled cavity 54 between the sled end walls 48 and 50.

A bias means in the form of an elongated compression spring 56 is disposed about the lead screw 46 within the sled cavity 54, and its opposite ends are engaged upon the pointer 52 and the sled end wall 48.

Once the sled 28 is attached to the suture 22, for example, it will be constrained against longitudinal movement relative to the frame 30. Rotation of the thumbwheel 44 in one direction will develop an increasing bias upon the sled 28 as the pointer 52 moves from the position of FIG. 10 to that of FIG. 11, tending to move the sled 28 proximally to increase the tension on the suture 22. Rotation of the thumbwheel 44 in the opposite direction develops a decreasing bias on the sled, tending to decrease the tension in the suture 22.

Pointer 52 is visible in FIG. 3 through an elongated slot 58 provided in the sled 28. Force indicia 60 is linearly disposed along a margin of the slot 58 and, in association with the pointer 52, yield an indication of the bias force developed upon the sled 28.

The present invention provides two means for indicating the longitudinal position of the sled 28 relative to the frame 30, one involving use of a linear scale, while the other involves an expanded circular scale. The linear version is best seen in FIG. 9 and comprises linearly arranged displacement indicia 62 engraved upon one of the frame side walls 32, and cooperative with an indicia or index 64 engraved upon the sled 28.

The circular expanded displacement scale is seen in FIGS. 3, 10 and 11. The instrument frame is modified to include an arcuate portion 64 having an engraved indicia or index 66 and an arcuate recessed ledge (not shown). This ledge rotatably seats and supports the edge margin of a circular dial face 68 which carries circularly arranged displacement indicia 70. Although not illustrated in detail, dial face 68 is integral with a transverse shaft (not shown) which is rotatably carried by the instrument frame and integrally associated with a pinion gear 72. In this version of the present instrument, the sled is modified to include an elongated recess which receives a rack 74 whose teeth are meshed with the teeth of the pinion gear 72. A gear ratio is preferably selected such that a predetermined amount of longitudinal movement of the sled relative to the instrument frame produces a greater change in the relative displacement of the indicia 66 and 70 as compared to the relative displacement of the indicia of the linear arrangement of FIG. 9. This makes the amount of sled displacement easier to read.

During certain graft tests, such as for joint laxity, it is useful to provide a means for fixing the sled 28 against longitudinal movement relative to the frame 30. As seen in FIG. 1, this can be accomplished by rotation of a thumb screw 76 which is rotatably carried by a side wall 32 of the instrument frame, and which includes a support shaft inner end (not shown) that can be brought into binding engagement with the sled 28 upon rotation of the thumb screw 76.

Although not shown, the sled cavity 54 is covered by a sled plate attached to the sled by suitable screws (not shown) to retain in position the components contained within the cavity 54.

The instrument 10 is adapted to accept or include a variety of attachments for locating or verifying the graft isometric path and for providing skeletal mounting and graft tensioning. As will be seen, some of these attachments are used in determining the proper or isometric path for the suture 22, while others are adapted for use in testing of the graft.

As seen in FIG. 3, the end wall 34 of the frame 30 includes an opening to separably accept the tubular shank of a nose piece 78. The nose piece 78 includes a head or circular flange which engages the inner face of the end wall 34 to maintain the nose piece 78 in position.

The diameter of the opening in the nose piece 78 is sufficiently large to slidably and removably accept the proximal extremity of a tubular suture nose 80 having an annular flange which seats against the end of the nose piece 78. The suture nose 80 includes a tubular extension 82 which, as seen in FIG. 2, is adapted to fit within the tunnel or suture opening 20 in the tibia 14 to skeletally mount or fix the frame 30 against movement.

An alternate version of the nose piece 78, indicated at 78a in FIG. 8, includes an integral transverse bracket 84 having a central opening aligned with the opening in the frame end wall 34. The extremities of the bracket 84 include laterally open slots adapted to removably fit within the annular grooves of a pair of posts 86 attached in spaced relation to the instrument frame. This post and bracket arrangement is simply a different way of mounting a suture nose piece. Other equivalent arrangements will suggest themselves to those skilled in the art.

The skeletal mounting or fixation provided by the nose pieces 78 and 78a is preferred but, if desired, fixation may be provided by a skeletal fixation angle or plate 88, as seen in FIGS. 5 and 17. With this arrangement, the nose piece 78 is removably fitted within an opening 90 in one leg of the plate 88, and the instrument frame is fixed against movement by attachment to the tibia of the other leg of the bracket 84 by a cortical screw 92. This arrangement thus requires dissection and provision of a tapped hole in the tibia.

Yet another form of skeletal fixation plate is illustrated in FIG. 7, the plate comprising a transverse element 94 which integrally mounts a cortical screw 96. The element 94 is characterized by laterally open slots 98 adapted to removably fit over the posts 86 of the post mount version of the instrument frame.

Since the nose piece 78 is readily removable, various sizes of nose pieces may be fitted to the frame 30 to fit within different sizes of suture or graft openings.

Two versions of suture or graft retaining means can be mounted to the sled end wall 50. One version is illustrated in FIG. 3 and comprises a retainer 100 having a longitudinal shank, and a transverse plate 102 which removably fits within a T-shaped slot provided in the sled end wall 50. The extremity of the retainer 100 includes lateral hook portions 104 about which a suture or graft can be looped or otherwise fitted for fixation in position by the hemostat 26.

The other or alternate form of suture or graft reretainer is illustrated at 100a in FIGS. 6, 10 and 11. Like retainer 100, the retainer 100a includes a shank and a plate 102 adapted to fit within the T-shaped slot of the sled distal wall 50. However, retainer 100a is characterized by side plates 106 which support a transverse shaft 108 which eccentrically and rotatably mounts a roller 110. If a graft is disposed beneath the roller 110 and toward the sled 28, and thence upwardly and reversely away from the sled 28, tensioning the graft tends to rotate the roller 110 in a clockwise direction, as viewed in FIG. 6. This traps the graft between the roller 110 and a lateral lower wall 112 of the retainer 100a thereby preventing separation of the graft from the retainer 100a.

When the proper location of the fixation sites has been determined through use of the suture 22, the final graft must be skeletally fixed temporarily to confirm this, and this must be done in such a way that permanent fixation is relatively easy. As seen in FIG. 4, a preferred means for temporarily skeletally mounting or fixing the instrument frame comprises a graft nose 114 which includes a centrally apertured transverse portion 116 adapted to be removably fitted over the protruding end of the nose piece 78. The graft nose 14 includes inwardly convergent sides 118 which terminate in a semicylindrical, laterally open extension 120 adapted to fit within a graft hole, such as is seen at 122 in FIG. 17.

The extension 120 is preferably nearly exactly semicircular in transverse cross section so that its maximum external diameter is only slightly less then the maximum internal diameter of the graft hole 122. There is then virtually no opportunity for lateral movement of the extension 120 within the graft hole 122, insuring exact centering of the graft within the graft hole 22.

In a typical procedure utilizing the method and instrument of the present invention a suture 22 is first fixed at the femoral fixation site 16. It is then passed through the suture opening 20 to the tibia fixation site 18.

According to the present skeletal referenced system, the instrument frame 30 must be temporarily skeletally fixed or mounted relative to the tibia 14. This can be done by cortical screw attachment to the tibia by using the plate 88 of FIG. 5 or the element 94 of FIG. 7. One of these is fitted over the nose piece 78, in one version of the instrument frame, or upon the posts 86 in the other version of the instrument frame. However, temporary skeletal mounting is preferably done by anchoring the frame 30 within the suture opening 20, which does not require dissection and provision of a tapped hole. With this arrangement the suture 22 is passed through the tubular extension 82 of the suture nose 80, and the nose 80 is then mounted to the nose piece 78 on the frame 30. The free end of the suture 22 is then disposed about the hook portions 104 of the retainer 100 and fixed by the hemostat 26.

Thumbwheel 44 is next operated to develop tension in the suture 22 and thereby hold the instrument in position. With the knee in 90 degrees of flexion, as illustrated in FIG. 12, thumbwheel 44 is operated to develop a test tension in the suture 22 of six pounds, for example, as indicated by the pointer 52. At this time the position of the sled 28 relative to the frame 30, that is, the graft displacement, is noted from the dial face of FIG. 3 or, in the version of FIG. 9, from the linear scale. The knee is then placed in full extension, as seen in FIG. 13, and the thumbwheel 44 operated until a force scale reading of the same six pounds is achieved. The displacement scale is again noted to determine if any change occurred in the position of the sled relative to the instrument frame. If no substantial change occurred, or if it is within acceptable limits, such as approximately 3 millimeters, the fixation sites selected are confirmed as satisfactory. Otherwise, different fixation sites must be selected to compensate for the undesired displacement and the procedure repeated.

Assuming the selected fixation sites are acceptable, the suture opening 20 is enlarged sufficiently by drilling or the like to receive a graft 124.

In a manner similar to the orientation of the suture 22, the graft 124 is disposed through graft hole 122, is fixed at its femoral extremity by means of a cancellous bone screw or staple, as seen in FIG. 14, and is extended out of the tibial fixation site 18 and through the preferred graft nose 114. The nose 114 is then fitted onto the frame 30 and seated within the graft hole. The free end of the graft is then fixed to the sled 28 by means of sutures sewn into the graft, and graft displacement and tension is determined in the manner described in connection with the suture 22. In addition to verification of correct isometric positioning of the graft, the instrument 10 can also be used to evaluate graft tension change with range of knee motion. This is done by placing the knee in 90 degree flexion, as seen in FIG. 12. The thumbwheel 44 is operated to develop a six pound load on the graft and the reading on the displacement scale is noted. The knee is then extended to the position of FIG. 13 and the thumbwheel 44 operated until the displacement scale reading is the same as when the knee was in 90 degrees of flexion. The force scale at this time indicates the ligament load The instrument 10 can also be used to tension the ligament graft and assess the resulting joint laxity. To accomplish this, the knee is placed in the desired degree of flexion and the desired ligament load is developed by rotation of the thumbwheel 44. Thumb screw 76 is tightened to lock the sled 28 to the frame 30. Joint laxity can now be assessed either through manual tests or by use of an arthrometer.

After the graft tests are completed and optimum graft orientation has been confirmed, with proper tension still applied to the graft, the tibial end of the graft is reached through the central open portion of the graft nose 114 and a cortical screw assembly 126, such as that seen in FIG. 17, is employed to fix the graft at the tibial fixation site, as seen in FIG. 15. The graft is then severed and the instrument 10 removed, as seen in FIG. 16.

From the foregoing it will be apparent that the method and instrument of the present invention enable objective isometric positioning and skeletal referenced tensioning of ligament grafts such as the anterior cruciate ligament.

By reason of the skeletal mounting of the instrument frame 30 at the fixation site, measurement of ligament graft length changes with constant force may be obtained by incremental force correction at varying degrees of knee flexion, and measurement of ligament graft tension changes with constant graft length may be obtained by incremental length correction at varying degrees of knee flexion and, finally, the graft can be tensioned and affixed in its tensioned state prior to removal of the instrument, whereby the tensioned graft closely approximates the dynamics of the contralateral knee.

Various modifications and changes may be made with regard to the foregoing detailed description without departing from the spirit of the invention.

We claim:

1. A method for establishing skeletal referenced isometric positioning and tensioning of a ligament graft between fixation sites on a pair of articulated bones, said method comprising the steps of:

establishing the locations of said fixation sites;

drilling openings in said bones between said fixation sites;

skeletally fixing a first portion of an instrument adjacent one of said fixation sites;

disposing a tension element through said openings, temporarily fixing one end of said element at the other of said fixation sites, and temporarily fixing the other end of said element to a second portion of said instrument which is movable relative to said first portion for displacement of said element.

determining the amount of the movement of said second portion relative to said first portion, and the amount of said bias to establish the amount of said displacement and tension during flexion of said bones and, if necessary, reestablishing said fixation sites and openings until said amount of said displacement and said tension satisfy predetermined criteria;

drilling larger graft openings in said bones between the established fixation sites;

repeating the foregoing skeletally fixing, disposing and determining steps relative to said graft; and fixing said graft to the established fixation sites.

2. A method for establishing skeletal referenced isometric positioning and tensioning of a cruciate knee ligament graft between femoral and tibial fixation sites, said method comprising the steps of:

approximating the location of said fixation sites;

drilling openings in the femur and tibia between said fixation sites;

skeletally fixing a first portion of an instrument adjacent one of said fixation sites;

disposing a tension element through said openings, temporarily fixing one end of said element at the other of said fixation sites, and temporarily fixing the other end of said element to a second portion of said instrument which is movable relative to said first portion for displacement of said element.

moving said second portion relative to said first portion against a bias to develop tension in said element;

determining the amount of the movement of said second portion relative to said first portion, and the amount of said bias to establish the amount of said displacement and tension during knee flexion and, if necessary, reestablishing said fixation sites and openings until said amount of said displacement and said tension remain substantially constant throughout said flexion;

drilling larger graft openings in said femur and tibia between the established fixation sites;

repeating the foregoing skeletally fixing, disposing and determining steps relative to said graft; and fixing said graft to the established femoral and tibial fixation sites.

3. An instrument for use in establishing skeletal referenced isometric positioning and tensioning of a ligament graft which passes between fixation sites on a pair of articulated bones, said instrument comprising:

an elongated frame having nose means operative to effect skeletal engagement of said frame adjacent one of the fixation sites, said frame further having elongated sled guide means;

a sled longitudinally slidable upon said sled guide means;

graft retaining means carried by said sled and operative to hold and fix, relative to said sled, the free end of a graft passing from the other of said fixation sites;

indicating means carried by said frame and said sled and cooperative to indicate the longitudinal position of said sled relative to said frame thereby to indicate any displacement of the graft;

bias development means carried by said frame and said sled and alternately operative to develop an increasing bias upon said sled to move said sled and increase the tension in the graft, or to develop a decreasing bias upon said sled to move said sled and decrease the tension in the graft; and sled fixing means carried by said frame and operative to fix said sled against movement relative to said frame.

4. An instrument according to claim 3 wherein said graft passes through drill holes in said bones, and said nose means comprises a tubuar nose through which said graft is movable, and wherein said tubular nose is adapted to seat within the drill hole adjacent said one of said fixation sites to effect said skeletal engagement.

5. An instrument according to claim 4 wherein said nose is laterally open and separably mounted to said frame whereby said nose is separable from said graft and from said frame subsequent fixation of the graft to said one of said fixation sites.

6. An instrument according to claim 3 wherein said graft passes through drill holes in said bones, and said nose means comprises a tubular nose through which said graft is movable, and wherein said tubular nose mounts a bracket adapted to receive a cortical screw to effect said skeletal engagement.

7. An instrument according to claim 3 wherein said sled includes a central cavity, and wherein said bias development means comprises: a threaded nut rotatably carried by said frame; a lead screw threadably engaged by said nut and terminating in an abutment element located in said cavity; and a compression spring having its opposite ends engaged upon said abutment element and said sled, respectively.

8. An instrument according to claim 7 wherein said sled carries force indicia, and said abutment element constitutes an indicator movable relative to said force indicia to establish the level of said tension in the graft.

9. An instrument according to claim 3 wherein said indicating means comprises indicia on said frame and said sled to indicate said longitudinal position of said sled relative to said frame.

10. An instrument according to claim 3 wherein said indicating means comprises: a rack on said sled; and a gear carried by said frame, meshed with said rack and having a dial face, said dial face and said frame including indicia cooperative to indicate said longitudinal position of said sled relative to said frame.

11. A method for establishing skeletal referenced isometric positioning and tensioning of an anterior cruciate knee ligament graft between femoral and tibial fixation sites, said method comprising the steps of:

approximating the location of said fixation sites;

drilling suture openings in the femur and tibia between said fixation sites;

inserting into the tibial suture opening a nose portion of an instrument frame to skeletally fix said frame adjacent said tibial fixation site;

disposing a suture through said openings and said nose portion, temporarily fixing one end of said suture at said femoral fixation site, and temporarily fixing the other end of said suture to a sled which is movable on said frame for longitudinally displacing said suture, the movement of said sled relative to said frame being through a bias means to develop a determinable tension in said suture;

determining the amount of said displacement and tension during knee flexion and, if necessary, reestablishing said fixation sites and suture openings until said amount of said displacement and said tension remain substantially constant throughout said flexion;

enlarging said suture openings between the finally established fixation sites to form graft openings;

repeating the foregoing inserting, disposing and determining steps relative to said graft;

fixing said graft to the established femoral and tibial fixation sites; and separating said nose portion from said graft.

12. An instrument for use in establishing skeletal referenced isometric positioning and tensioning of a cruciate knee ligament graft which passes through holes extending between femoral and tibial fixation sites, said instrument comprising:

an elongated frame having a nose portion receivable in the hole adjacent said tibial fixation site to skeletally fix said frame adjacent said tibial fixation site, said frame further having elongated sled guide means;

a threaded nut rotatably carried by said frame;

a lead screw threadably engaged by said nut and terminating in an abutment element;

a sled longitudinally slidable upon said sled guide means and relative to said lead screw, and including a central cavity receiving said abutment element, said sled including force indicia cooperative with said abutment element to indicate the longitudinal position of said abutment element relative to said sled;

graft retaining means carried by said sled and operative to hold and fix, relative to said sled, the free end of a graft passing from said femoral fixation site and through said distal nose portion;

displacement indicating means carried by said frame and said sled and cooperative to indicate the longitudinal position of said sled relative to said frame thereby to indicate any displacement of the graft;

a compression spring carried by and having its opposite ends engaged upon said abutment element and said sled, respectively, said nut being operative in one direction to develop an increasing bias upon said sled to move said sled and increase the tension in the graft, and operative in the opposite direction to develop a decreasing bias upon said sled to move said sled and decrease the tension in the graft, the relative position of said abutment element and said force indicia indicating the amount of tension in the graft; and sled fixing means carried by said frame and operative to fix said sled against movement relative to said frame.

13. An instrument according to claim 12 wherein said nose portion is laterally open and separably mounted to said frame whereby said nose is laterally separable from said graft and from said frame subsequent fixation of the graft to said tibial fixation site.

14. An instrument according to claim 12 wherein said displacement indicating means comprises indicia on said frame and said sled to indicate said longitudinal position of said sled relative to said frame.

15. An instrument according to claim 12 wherein said displacement indicating means comprises: a rack on said sled; and a gear carried by said frame, meshed with said rack and having a dial face, said dial face and said frame including indicia cooperative to indicate said longitudinal position of said sled relative to said frame.

* * * * *